United States Patent
Liu

(10) Patent No.: US 8,178,344 B2
(45) Date of Patent: May 15, 2012

(54) SYSTEM AND METHOD FOR ANTIGEN STRUCTURE-INDEPENDENT DETECTION OF ANTIGENS CAPTURED ON ANTIBODY ARRAYS

(76) Inventor: George Dacai Liu, Collegeville, PA (US)

( * ) Notice: Subject to any disclaimer, the term of this patent is extended or adjusted under 35 U.S.C. 154(b) by 99 days.

(21) Appl. No.: 12/854,191

(22) Filed: Aug. 11, 2010

(65) Prior Publication Data
US 2010/0304999 A1 Dec. 2, 2010

Related U.S. Application Data

(62) Division of application No. 10/870,766, filed on Jun. 17, 2004, now Pat. No. 7,799,556.

(51) Int. Cl.
*C12M 1/34* (2006.01)
*C12M 3/00* (2006.01)
(52) U.S. Cl. ........... 435/287.2; 435/7.1; 435/7.94; 435/283.1; 435/288.3; 435/288.7; 436/501; 436/518; 436/524
(58) Field of Classification Search .......... 435/7.1, 435/7.94, 283.1, 287.1, 287.2, 288.3, 288.7; 436/501, 518, 524
See application file for complete search history.

(56) References Cited

U.S. PATENT DOCUMENTS

| 4,143,124 A | 3/1979 | Masson et al. |
| 4,567,041 A * | 1/1986 | Likhite ................ 530/389.5 |
| 4,882,423 A | 11/1989 | Taguchi et al. |
| 5,252,461 A | 10/1993 | Weisbart |
| 5,686,315 A * | 11/1997 | Pronovost et al. ............ 436/510 |
| 6,630,584 B1 * | 10/2003 | Solomon et al. ............. 536/24.5 |
| 6,942,977 B1 * | 9/2005 | Newman et al. ............... 435/7.1 |
| 2001/0001061 A1 * | 5/2001 | Prusiner et al. ............. 435/7.92 |
| 2002/0127623 A1 * | 9/2002 | Minshull et al. ............. 435/7.92 |
| 2003/0003516 A1 * | 1/2003 | Robinson et al. ............. 435/7.9 |
| 2003/0153013 A1 | 8/2003 | Huang |
| 2004/0067539 A1 | 4/2004 | Carlsson et al. |
| 2004/0203084 A1 * | 10/2004 | Levinson ..................... 435/7.92 |
| 2005/0048545 A1 * | 3/2005 | Cull et al. ........................ 435/6 |

OTHER PUBLICATIONS

Duncan et al., The binding site for C1q on IgG, Letters to Nature, 1988, vol. 332, p. 738-740.*
Kaul and Loos, Dissection of C1q capability of interacting with IgG, JBC, 1997, 272:33234-33244.
Marques et al., Arginine residues of the globular regions of human C1q involved in the interaction with immunoglobulin G, JBC, 1993, 268:10393-10402.

* cited by examiner

*Primary Examiner* — Melanie J Yu
(74) *Attorney, Agent, or Firm* — George Liu

(57) ABSTRACT

The present invention provides a system and method for detecting antigens captured on an antibody array. The method comprises the following steps of providing the antibody array having at least two antibodies, contacting the antibody array with a sample containing at least one antigen that may be captured by the antibodies disposed on the antibody array, and detecting the at least one antigen captured by the antibody array with a detecting agent that specifically binds to the antigen-bound antibodies on the antibody array, thereby the at least one antigen captured by the antibody array can be detected independent of the structures of the antigens. In a preferred embodiment, C1q is used as the detecting agent to detect antigen-bound antibodies.

8 Claims, No Drawings

US 8,178,344 B2

SYSTEM AND METHOD FOR ANTIGEN STRUCTURE-INDEPENDENT DETECTION OF ANTIGENS CAPTURED ON ANTIBODY ARRAYS

RELATED APPLICATIONS

This application is a divisional application of U.S. patent application Ser. No. 10/870,766, filed Jun. 17, 2004 now U.S. Pat. No. 7,799,556.

FIELD OF THE INVENTION

The present invention generally relates to antibody arrays, and more particularly to systems and methods for antigen structure-independent detection of antigens captured on antibody arrays.

BACKGROUND OF THE INVENTION

Microarray technology has become a crucial tool for large-scale and high-throughput biology. A protein-detecting microarray comprises many different affinity reagents (frequently antibodies) arrayed at high spatial density on a solid support. Each agent captures its target protein from a complex mixture (such as serum or cell lysate), and the captured proteins are subsequently detected and quantified. The protein microarray format enables fast, easy and parallel detection of thousands of addressable proteins and side-by-side measurements. It may be applied to analyze antibody-antigen, protein-protein, protein-nucleic acid, protein-lipid and protein-small-molecule interactions, as well as enzyme-substrate interactions.

Currently, the captured proteins in an antibody array are detected in two ways. One is a sandwich immunoassay in which capture antibodies are immobilized on the solid support, and the bound proteins are detected using a second, labeled detection antibody. For example, Huang et al. (Anal. Biochem. 2001, 294:55-62) described an ECL based immunoassay array for the simultaneous assay of 24 cytokines from either cultured media or patient sera. The system was based on the standard sandwich ELISA technology but the initial capture antibodies raised to the various cytokines were transferred in an ordered format onto a membrane. It is evident that this type of antibody array is a simple collection of multiple individual ELISA assays. Another is an antigen capture assay in which proteins are similarly captured by immobilized antibodies, but the captured proteins are detected directly. For example, Haab et al. (Genome Biol., 2001, 2research0004.1-0004.13) labeled two samples independently with distinguishable fluorophores and mixed the samples before applying them to the array. However, this method does not offer signal amplification beyond that provided by the use of fluorophores. In addition, the labeling is time consuming and some proteins may be labeled preferentially on their antigenic epitopes and lose their ability to be captured by their affinity reagents.

Therefore, there is an imperative need to have a system and method of detecting antigens captured on an antibody array, wherein the system and method overcome most, if not all, of the limitations in the prior arts. This invention satisfies this need by disclosing a system and method of detecting antigens captured on an antibody array that are independent of antigen structures. Other advantages of this invention will be apparent with reference to the detailed description.

SUMMARY OF THE INVENTION

The present invention provides a system and method for detecting antigens captured on an antibody array. The method comprises the following steps of providing the antibody array having at least two antibodies, contacting the antibody array with a sample containing at least one antigen that may be captured by the antibodies disposed on the antibody array, and detecting the at least one antigen captured by the antibody array with a detecting agent that specifically binds to the antigen-bound antibodies on the antibody array, thereby the at least one antigen captured by the antibody array can be detected independent of the structures of the antigens. In a preferred embodiment, C1q is used as the detecting agent to detect antigen-bound antibodies.

Accordingly, one object of the present invention is to provide systems and methods for their applications in proteomics, wherein the systems and methods are highly specific and sensitive, and easily adapted to automation.

The objectives and advantages of the invention will become apparent from the following detailed description of preferred embodiments thereof.

DETAILED DESCRIPTION OF THE INVENTION

The present invention may be understood more readily by reference to the following detailed description of certain embodiments of the invention.

Throughout this application, where publications are referenced, the disclosures of these publications are hereby incorporated by reference, in their entireties, into this application in order to more fully describe the state of art to which this invention pertains.

The present invention provides systems and methods of utilizing an antibody array for simultaneously detecting different antigens regardless of the antigen structures. The practice of the present invention will employ, unless otherwise indicated, conventional techniques of molecular biology (including recombinant techniques), microbiology, cell biology, biochemistry and immunology, which are known to those skilled in the art. For example, monoclonal and polyclonal antibodies can be produced for different antigens in different hosts by known methods. The manipulation of the antibodies is also known. In addition, the production and preparation of antigens are also known to those skilled in the art. Thus, no citation to or detailed description of the known techniques will be given herein for the sake of brevity.

It is common that one molecule or one class of molecules can be induced to perform certain similar, if not identical, function(s) by the interactions (e.g., binding) with different entities, regardless of the structures of the entities interacted with the molecule(s). The typical molecules are the antibodies in animals including mouse, rat, rabbit, pig, goat, horse, dog and human beings. For example, when IgGs are bound by their antigens, the IgGs will go conformational changes so that the first component of the classical complement pathway, C1q, can bind to the IgGs, resulting in the activation of the classical complement pathway. It is reasoned that all the antigen-bound IgGs must share at least one conformational epitope that is recognized by the C1q. More importantly, different antigens can induce the shared conformational epitopes regardless of the antigen structures. Therefore, an antigen bound to its corresponding antibody can be detected by detecting of the conformational changes on the antibody instead of the identity of the antigen. One of the evident applications of this finding is to antibody arrays wherein antigens captured by the immobilized antibodies can be detected by a single or few detecting agents that recognize the shared conformational epitopes on the antibodies. The obvious advantages include no more requirements of paired antibodies for each antigen and no more cocktails of second antibodies for each antigen to be detected on an antibody array.

Throughout the present application, antibody, antigen, antibody array and detecting agents are used for the simplicity of description. "Antibody" as ud herein is intended to cover any molecule or any class of molecules on which at least one shared conformational epitope can be induced by two or more different antigens. It is to be noted that the definition is function-based. While the examples illustrate the induction of new conformational epitopes recognized by C1q, it is to be appreciated that the loss of conformational epitopes on antigen-bound antibodies may also be utilized to detect and/or verify the binding of antigens. The induced or lost conformational epitopes on an antigen-bound antibody shared by at least two antibodies are referred herein as "shared conformational epitopes." An applicable antibody may include conventional antibodies, antibody mimics and receptors. The conventional antibodies can encompass monoclonal, polyclonal antibodies, chimeric antibodies, single chain, and mutants thereof. Antibodies may be murine, rat, rabbit, chicken, human, or any other origin (including humanized antibodies). General techniques for antibodies are known in the art.

"Antigen" as used herein refers to any entity that binds to an antibody disposed on an antibody array and induces at least one shared conformational epitope on the antibody. Antigens could be proteins, peptides, antibodies, small molecules, lipid, carbohydrates, nucleic acid, and allergens. An antigen may be in its pure form or in a sample in which the antigen is mixed with other components.

"Antibody array" as used herein refers to a linear or two-dimensional array of two or more different antibodies formed on the surface of a solid support.

"Detecting agent" as used herein refers to any molecule that has the ability to selectively bind to immobilized antibodies on an antibody array that have at least one shared conformational epitope resulting from the binding of antigens. The detecting agent will not bind, or bind at an insignificant level the antibodies immobilized on an antibody array if the antibodies are not bound with their correspondingly antigens. The shared conformational epitopes may be new ones induced by the antigens or lost ones destroyed by the antigens. The detecting agent includes proteins (e.g., C1q, RF), peptides (C1q fragments), and antibodies that specifically recognize the shared conformational epitopes.

In one preferred embodiment of the present invention, there is provided an antibody array system for detecting antigens captured on the antibody array. The system comprises an antibody array of two or more antibodies for antigens, and at least one detecting agent that is able to recognize at least one shared conformational epitope on the antibodies resulting from the binding of the antigens.

An antibody array is an ordered spatial arrangement of two or more antibodies on a physical substrate. Row and column arrangements are preferred due to the relative simplicity in making and assessing such arrangements. The spatial arrangement can, however, be essentially any form selected by the user, and preferably but need not be, in a pattern. The most common form of antibody arrays is that antibodies that bind specific antigens are arrayed on a glass slide at high density. A sample containing possible antigens is passed over the array and the bound antigen is detected after washing.

The antibodies in an antibody any are preferably printed onto a solid support. Amongst the large number of solid-support materials applicable for the production of antibody arrays, silica or glass is most often used because of its great chemical resistance against solvents, its mechanical stability, its low intrinsic fluorescence properties, and its flexibility of being readily functionalized. Examples of well known solid supports include polypropylene, polystyerene, polyethylene, dextran, nylon, amylases, glass, natural and modified celluloses, polyacrylamides, agaroses and magnetite. Those skilled in the art will know of other suitable solid support for binding antibodies, or will be able to ascertain such, using routine experimentation.

Antibodies may be immobilized onto a support surface either by chemical ligation through a covalent bond or non-covalent binding. There are many known methods for covalently immobilizing antibodies onto a solid support. For example, MacBeath et al. (J Am Chem Soc, 1999, 121:7967-7968) use Michael addition to link thiol-containing compounds to maleimide-derivatized glass slides to form a microarray of small molecules. See also, Lam and Renil, Current Opinion in Chemical Biology, 2002, 6:353-358.

Antibodies may be attached to various kinds of surface via diffusion, adsorption/absorption, covalent cross-linking and affinity. Antibodies may be directly spotted onto plain glass surface. To keep antibodies in a wet environment during the printing process, high percent glycerol (30-40%) may be used in sample buffer and the spotting is carried out in a humidity-controlled environment.

The surface of a substrate may be modified to achieve better binding capacity. For example, the glass surface may be coated with a thin nitrocellulose membrane or poly-L-lysine such that antibodies can be passively adsorbed to the modified surface through non-specific interactions. In addition, streptavidin may be arrayed onto solid surfaces for capture of biotinylated proteins.

Antibody arrays can be fabricated by the transfer of antibodies onto the solid surface in an organized high-density format followed by chemical immobilization. The techniques for fabrication of an array include, but are not limited to, photolithography, ink jet and contact printing, liquid dispensing and piezoelectrics. The patterns and dimensions of antibody arrays are to be determined by each specific application. The sizes of each antibody spots may be easily controlled by the users.

As discussed above, the present invention takes advantage of the shared conformational epitopes on antibodies resulting from the binding of antigens. The shared conformational epitopes can be induced or destroyed by different antigenic epitopes from one antigen or different antigenic epitopes from different antigens. The detecting agent of the present invention is capable of recognizing at least one shared conformational epitope present in all antigen-bound antibodies in an antibody array so that the detection of antigens bound to an antibody array is independent of the structure of the antigens. The nature of the detecting agent is not important for the present invention as long as the detecting agent is applicable for the present invention.

In one preferred embodiment, the present invention provides the detecting agents including complement 1q (C1q) and rheumatoid factor (RF). Both C1q and RF have the property of binding to antibodies that are part of complexes formed between antibodies and antigens, but essentially do not bind to non-complexed antibodies. Both C1q and RF have been used to measure circulating immune complexes. See, U.S. Pat. No. 4,143,124; and PCT, WO 97/01758. C1q is the first component of the classical complement cascade pathway, which is commonly present in animals including mouse, rat, rabbit, sheep, goat, horse, cattle, dog and human beings. C1q shares high homology with similar structures from different species and has cross species activities. Thus, C1q applicable in the present invention is not limited to any C1q from a specific species. For example, human C1q is a glycoprotein of about 460 kDa. In its electron microscopy image C1q appears as a bunch of tulips, with six globular heads, each connected by a stalk to a central bundle of fibers. One C1q molecule is composed of 18 polypeptide chains. The chains are of three different types named A, B, and C, of 29, 27, and 23 kDa, respectively. They are linked by disulfide bonds to form six A-B and three C-C dimers. Each of the six individual segments of C1q comprises one chain of each type, which acquire a triple helical structure in the fibrillar region. See, e.g., Kaul and Loos, The Journal of Biological Chemistry, 1997, 272:33234-33244.

C1q binds to antibodies in antigen-antibody complexes, but not free antibodies. The binding of C1q to antibodies may be optimized by exploring incubation time, incubation temperature, pH values, and ionic strengths. The optimized conditions for each antibody array can be obtained with methods well known to those skilled in the art. See, Tan et al., Proc. Natl. Acad. Sci. USA, 1990, 87:162-166; Marques et al., The Journal of Biological Chemistry, 1993, 268:10393-10402.

In addition, some portions or fragments of C1q have retained the capacity of binding to antigen-bound antibodies. Thus, C1q as used herein includes any C1q portions or fragments that retain the capacity of binding to antigen-bound antibodies. Fragments of C1q and peptides prepared synthetically are described in WO 92/07267.

Rheumatoid factors (RF) are antiglobulin antibodies that bind IgG immunoglobulins and are found in the serum and synovial fluid of most patients with rheumatoid arthritis. Certain RFs can bind to neoantigens created within IgG by the formation of antigen-antibody immune complexes. See, U.S. Pat. No. 5,252,461. RF is a known material and methods for its preparation and isolation is known. See, U.S. Pat. No. 4,143,124. A portion or fragment of RF can also be used for this invention if it retains its binding capacity. See, PCT/DK96/00288.

In one preferred embodiment, the present invention provides methods for detecting the antigens bound to the antibody array as described hereinabove. Briefly, the methods comprise the steps of providing an antibody array, contacting the array with a sample containing antigens, and detecting the bound antigens by using the detecting molecules against the antibodies. The process can be done manually and/or automatically. The handling of arrays is well known to those skilled in the art.

As used herein, "sample" encompasses a variety of sample types and/or origins, such as blood and other liquid samples of biological origin, solid tissue samples such as a biopsy specimen or tissue cultures or cells derived therefrom, and the progeny thereof. The term "sample" encompasses a clinical sample, aryl also includes cells in culture, cell supernatants, cell lysates, serum, plasma, biological fluid, and a pure or enriched bacterial or viral sample derived from any of these, for example, as when a sample is cultured in order to increase, enrich and/or substantially purify a bacterial or viral sample therefrom. A sample can be from microorganisms, e.g., bacteria, yeasts, viruses, viroids, molds, fungi, plants, animals, including mammals such as humans. A sample may comprise a single cell or more than a single cell. These samples can be prepared by methods known in the art such as lysing, fractionation, purification, including affinity purification, FACS, laser capture microdissection or iospycnic centrigugation.

When the antibody array is contacted with a sample, the formation of antibody:antigen complexes can be performed under a variety of conditions. It is also true for the reaction of the detecting molecules with the antibodies. The reaction solutions can contain varying degrees of salt or have varying pH values. In addition, the binding reaction can be carried out at varying temperature. In general, pH conditions will range from 2-10 (most preferably around pH7), temperatures from 4-45° C. (preferably 15-30° C.) and salt conditions from 1 µm to 5M (in the case of NaCl).

The readout of the detecting agents bound to the antibodies in an antibody array can take up many forms. Prior to description of the readout methods, it is to be appreciated that the antigens in a sample and the second detecting molecules (e.g., antibodies against the detecting molecules such as anti-C1q antibodies) against the detecting agents can be detectably labeled and detected as the detecting agents as described hereinafter. For example, the antigens in a sample can be labeled with fluorescent dyes or detected by their specific antibodies in combination with the detecting agents to quantify and/or verify the binding antigens. Therefore, the detection methods for detecting agents may be compatible with other immunoassays as users desire.

The term "detectably labeled" as used herein is intended to encompass antigen or detecting agent directly coupled to a detectable substance, such as a fluorescent dye, and antigen or detecting agent coupled to a member of binding pair, such as biotin/streptavidin, or an epitope tag that can specifically interact with a molecule that can be detected, such as by producing a colored substrate or fluorescence.

Fluorescence detection methods are generally the preferred detection method because they are simple, safe, extremely sensitive and can have very high resolution. Typically, an antibody array is either directly probed with a fluorescent detecting molecule or in two step by first using a tagged probe (e.g., biotin), which can then be detected in a second step using a fluorescently labeled affinity reagent (e.g., streptavidin).

A biotin labeled target can be detected by gold-conjugated streptavidin with silver enhance solution so that the resultant black image of microarray spots can be easily detected with a commercial CCD camera.

The detecting agents (e.g., C1q and RF) and anti-detecting agent antibodies may be attached by the 5' end of an oligonucleotide primer. Then the signals may be significantly increased by Rolling circle amplification (RCA). In the presence of a DNA circle, DNA polymerase and nucleotides, rolling circle replication generates a concatamer of circle DNA sequence copies that remain attached to the antibody. The concatamer is then detected by the hybridization of fluorescent, complementary oligonucleotide probes. See, e.g., Schweitzer et al., Proc Natl Acad Sci USA 2000, 97:10113-10119.

C1q that binds to the antibody array can be detected using any means known in the art. In some embodiments, the C1q is labeled, using any methods known in the art. See, U.S. Pat. No. 4,882,423. For example, the C1q may be labeled with one or more labeling moieties including compositions that can be detected by photochemical, spectroscopic, biochemical, immunochemical, chemical, optical, electrical, bioelectronic, etc. means. For example, useful protein labels include radiolabels (e.g., 3H, 125I, 35S, 14C, or 32P), fluorescent dyes (e.g., fluorescein isothiocyanate, Texas red, rhodamine, and the like); electron-dense reagents, enzymes (e.g., LacZ, CAT, horse radish peroxidase, alkaline phosphatase and others, commonly used as detectable enzymes, either as marker gene products or in an ELISA); biotin, dioxigenin, or haptens and proteins for which antisera or monoclonal antibodies are available. A wide variety of labels and conjugation techniques are known and generally applicable to the present invention for the labeling of proteins.

Analysis of antigens bound to the antibody arrays can be quantitative, semi-quantitative or qualitative. "Detect" refers to identifying the presence, absence and/or amount of antigen to be detected. "Absence" of binding, and "lack of detection of product" as used herein includes insignificant or de minimus levels.

It is to be appreciated that the antibodies in an antibody array need not be characterized because no paired antibodies are required for the detection of the bound antigens in accordance with the present invention. In certain embodiments, arrays of uncharacterized antibodies may be used to compare the protein expression profiles of cells, for example, comparisons can be made between a population of cells from one tissue, and a second tissue, or from cells derived from a particular tissue but from different species. Comparisons can be made between normal cells and cells from the same tissue type that originate from an individual with a pathogenic disorder. For example, comparisons can be made between normal cells and cancer cells. Comparisons can additionally be made between cells in a resting state and cells in an activated state.

Detection and characterization of bacterial or viral infection is of crucial importance in the practice of clinical microbiology and in environmental testing, such as food safety and biohazard safety testing. In another embodiment, the disclosed arrays are useful for evaluating the expression of proteins by pathogens, such as, for example, bacteria, parasites, viruses, and the like. These antibodies have utility as diagnostic agents as well as potential therapeutics.

The systems and methods disclosed herein can be used in methods of diagnosing particular disorders. For example, in a diagnostic kit, a collection of antibodies specific for a range of antigens associated with one or more disorders can be arrayed and contacted with a bodily fluid containing antigens whose presence or absence would indicate a particular disorder. The advantage of using an array over a conventional immunoassay is the ability to include a population of antibodies diagnostic for a variety of disorders on a single surface, significantly reducing time, costs and materials needed to effect a diagnosis.

It is to be appreciated that many conventional procedures are not described herein including blocking and washing steps in performing the methods of the present invention. These procedures are well known to those in the art.

EXAMPLES

The following examples are offered by way of illustration and not by way of limitation.

Example 1

Murine monoclonal antibodies were raised against recombinant human prion proteins. Their specificity for recombinant prion proteins (PRP) including human and bovine was verified by ELISA and western blot. The antibodies were purified in accordance with standard techniques. A total of seven murine monoclonal antibodies against recombinant human PRP were used in the experiments described herein, Antibodies (7A12, 8B4, 2C2, 8H4 and 6H3) are IgG1 and antibodies (8F9 and 12H7) are IgG2b. Murine monoclonal antibodies against IL-2 and IL-4 were commercially available. Human C1q and Sheep anti-human C1q were purchased from Cortex Biochem Inc. (San Leandro, Calif.). Donkey anti-sheep IgG-HRP was purchased from Roche Applied Science (Indianapolis, Ind.).

The first experiment was intended to demonstrate that the immobilization of antibodies on the solid support does not cause C1q to bind to the immobilized antibodies, and to show that C1q is able to detect the specific binding of antigens to their antibodies.

The experiments described herein were done in accordance with conventional ELISA assays except for that the second antibody was substituted with C1q. Briefly, the antibodies were diluted in PBS (pH 7.4) to a concentration of 2 µg/ml. Each well of a 96-well plate was coated with 100 µl of diluted antibodies (anti-IL2, anti-IL4, and 7A12) for 3 hours at room temperature. Then coated wells were blocked with commercial blocking buffer for 1.5 hours at room temperature. After washing three times with PBST (PBS with 0.05% Tween-20), recombinant human prion proteins were added into each well (100 µl/well) at concentration of 2 µg/ml, and incubated for overnight at 4° C. After washing three times with PBST, human C1q was added into each well at concentrations of 2 µg/ml, 0.2 µg/ml, 0.02 µg/ml and 0 µg/ml and incubated for three hours at room temperature. After washing three times with PBST, sheep anti-human C1q antibodies were added into each well at concentration of 2 µg/ml and incubated for 1.5 hours at room temperature. After washing three times with PBST, donkey anti-sheep antibodies conjugated with HRP were added into each well (1/5000) and incubated for 1.5 hours at room temperature. Finally the wells were developed with ABTS for thirty minutes. The results were summarized in Table 1.

TABLE 1

Summary of OD reading under the conditions described above.

| [C1q] | ABs | | |
|---|---|---|---|
| | Anti-IL2 | Anti-IL4 | 7A12 |
| 0 | 0.085 | 0.1 | 0.115 |
| 0.02 | 0.09 | 0.1 | 0.155 |
| 0.2 | 0.09 | 0.1 | 0.16 |
| 2 | 0.09 | 0.11 | 0.2 |

Example 2

More anti-human PRP antibodies were tested for their conformational changes induced by their antigens. The procedure was the same as Example 1 except for that recombinant human prion proteins were added into each well (100 µl/well) at concentrations of 2 µg/ml, 0.2 µg/ml and 0 µg/ml, and that the C1q was tested in three concentrations instead of four.

The results are summarized in Table 2. The results demonstrated that C1q is able to distinguish the immobilized but free antibodies from the immobilized but bound with antigens. It is to be noted that some antibodies may not be suitable for the application of antibody arrays. As shown here, 8F9 is not suitable for such purpose. However, whether an antibody is suitable for the application of antibody array may be easily determined by routine experimentation.

TABLE 2

Summary of OD reading under the conditions as described above.

| | Abs | | | | | | | | |
|---|---|---|---|---|---|---|---|---|---|
| | 8B4 | | | 2C2 | | | 8H4 | | |
| | C1q | | | | | | | | |
| PRP | 0 | 0.2 | 2 | 0 | 0.2 | 2 | 0 | 0.2 | 2 |
| 0 | 0.041 | 0.054 | 0.048 | 0.059 | 0.057 | 0.066 | 0.145 | 0.147 | 0.156 |
| 0.2 | 0.041 | 0.092 | 0.218 | 0.067 | 0.185 | 0.506 | 0.141 | 0.22 | 0.294 |
| 2 | 0.043 | 0.08 | 0.22 | 0.066 | 0.152 | 0.441 | 0.14 | 0.169 | 0.222 |
| | Abs | | | | | | | | |
| | 8F9 | | | 6H3 | | | 12H7 | | |
| | C1q | | | | | | | | |
| PRP | 0 | 0.2 | 2 | 0 | 0.2 | 2 | 0 | 0.2 | 2 |
| 0 | 0.055 | 0.251 | 0.731 | 0.115 | 0.125 | 0.124 | 0.131 | 0.138 | 0.144 |
| 0.2 | 0.054 | 0.248 | 0.724 | 0.118 | 0.147 | 0.183 | 0.128 | 0.341 | 0.817 |
| 2 | 0.052 | 0.273 | 0.732 | 0.125 | 0.15 | 0.187 | 0.090 | 0.236 | 0.828 |

While the present invention has been described with reference to particular embodiments, it will be understood that the embodiments are illustrative and that the invention scope is not so limited. Alternative embodiments of the present invention will become apparent to those having ordinary skill in the art to which the present invention pertains. Such alternate embodiments are considered to be encompassed within the spirit and scope of the present invention. Accordingly, the scope of the present invention is described by the appended claims and is supported by the foregoing description.

What is claimed is:

1. A method for detecting antigens captured on an antibody array, comprising the following steps of:
providing the antibody array having at least two IgG antibodies, wherein each of the at least two IgG antibodies on the antibody array can be induced to present at least one shared conformational epitope when it is bound by its antigen(s);
contacting the antibody array with a sample containing at least one antigen that may be captured by the antibodies disposed on the antibody array; and
detecting the at least one antigen captured by the antibody array with a detecting agent that specifically binds to the at least two IgG antibodies that have been induced by their antigens with the at least one shared conformational epitope on the antibody array, thereby the at least one antigen captured by the antibody array can be detected independent of the structures of the antigens.

2. The method of claim 1, wherein the antibodies of the antibody array are from an animal or cells thereof.

3. The method of claim 2, wherein the animal is selected from the group consisting of mouse, rat, rabbit, sheep, goat, horse, bovine, dog and human.

4. The method of claim 1, wherein the antibodies of the antibody array are monoclonal antibodies.

5. The method of claim 1, wherein the at least antigen is one selected from the group consisting of proteins, peptides, glycoproteins, lipoproteins, lipids, nucleic acids, small molecules and allergens.

6. The method of claim 1, wherein the sample includes a clinical sample, and cultured cells, cell supernatants, cell lysates, serum, plasma, biological fluid, and a pure or enriched bacterial or viral sample derived from any of these.

7. The method of claim 1, wherein the detecting agent is a protein or antibody or, portions or fragments thereof.

8. The method of claim 1, wherein the detecting agent is C1q or, portions or fragments thereof.

* * * * *